(12) United States Patent
Huang

(10) Patent No.: US 7,371,226 B2
(45) Date of Patent: May 13, 2008

(54) PLUNGER OF A SYRINGE

(76) Inventor: Hung Chi Huang, 235 Chung-Ho Box 8-24, Taipei (TW)

( * ) Notice: Subject to any disclaimer, the term of this patent is extended or adjusted under 35 U.S.C. 154(b) by 224 days.

(21) Appl. No.: 11/166,946

(22) Filed: Jun. 27, 2005

(65) Prior Publication Data

US 2008/0009795 A1    Jan. 10, 2008

(51) Int. Cl.
*A61M 5/00* (2006.01)
(52) U.S. Cl. ............................................. 604/110
(58) Field of Classification Search ............... 604/124, 604/207, 218, 221–222, 228, 110, 181, 186, 604/187, 192, 197
See application file for complete search history.

(56) References Cited

U.S. PATENT DOCUMENTS 5,242,400 A * 9/1993 Blake et al. ................ 604/110
5,575,774 A * 11/1996 Chen ........................... 604/110
6,488,656 B1 * 12/2002 Wu .............................. 604/110
6,921,382 B2 * 7/2005 Lee et al. .................... 604/110

* cited by examiner

*Primary Examiner*—Manuel Mendez

(57) ABSTRACT

A plunger of a syringe characterized by a hook unit formed integrally at the front end of the stopper of thereof. The hook unit comprises a central rod and a push wing extended outwardly from a lateral wall of the central rod. The push wing can be attached to the central rod by a lateral force, which is urged during an insertion process, so that the hook unit will be inserted into a receptacle formed at the rear end of the needle hub in the axial direction. The receptacle has an entrance hole and a cavity lager then the hole, whereby the flexible push wing will be extended again after the unit is in the cavity, forming a locked configuration. As the plunger is pulled back, the needle mount will be pulled into the needle barrel accordingly, achieving a function of self destruction.

7 Claims, 3 Drawing Sheets

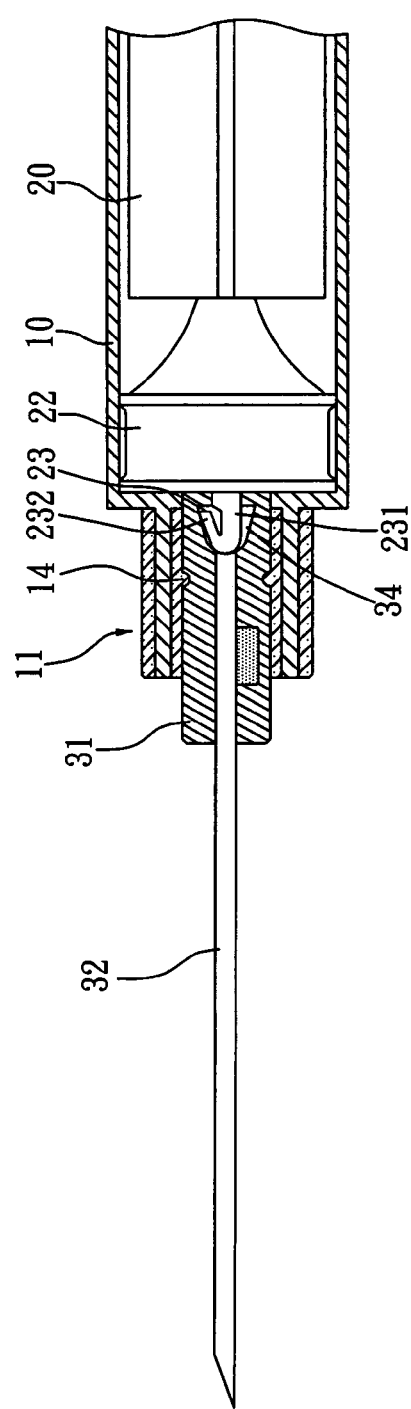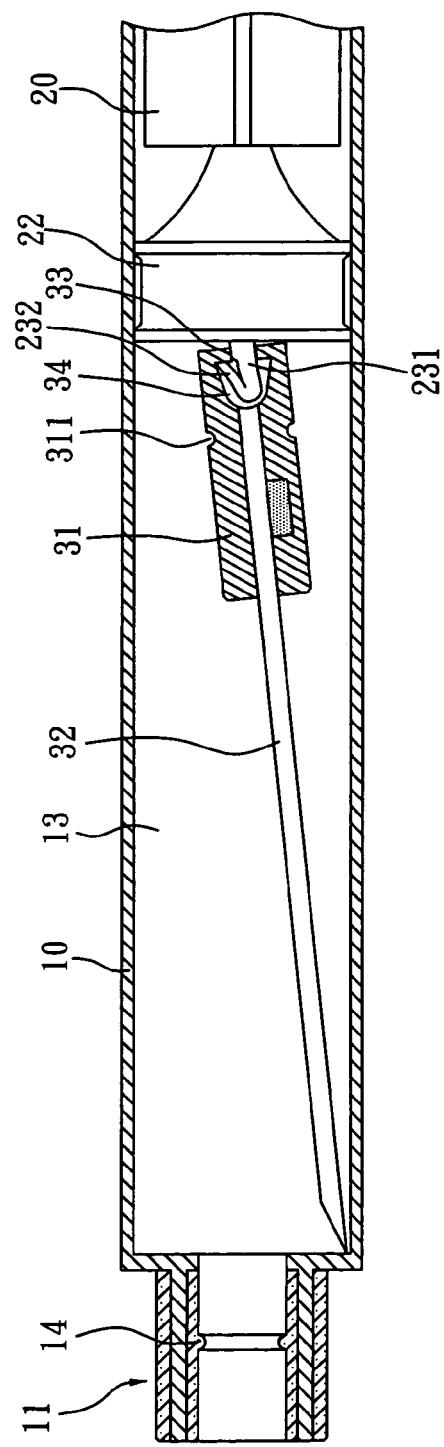

PLUNGER OF A SYRINGE

FIELD OF THE INVENTION

The present invention relates to plungers used in syringes, more particularly to a plunger of a syringe characterized by a hook unit formed integrally at the front end of the stopper of thereof. Thereby, the present invention can achieve a function of self destruction with a simple and reliable structure.

BACKGROUND OF THE INVENTION

A safety syringe of the prior art emphasizes the function that the needle thereof will be pulled back into the syringe barrel by a link rod after being used. However, such a structure cannot destroy the needle completely.

A safety syringe of rotational contraction of the prior art can attain the goal of single usage; but it is quiet costly to manufacture and cannot be immune from the possibility of being used again. The safety syringe of rotational contraction has a hook portion in the front of a needle barrel for forming a granular support against a needle hub. A receptacle is formed at the rear end of the needle hub, which receptacle has a small neck portion, whereby a conic head in the front of a push rod will be locked within the receptacle. The conic surface of the head is further provided with a plurality of projected teeth for engaging corresponding holes on the inner wall of the receptacle, whereby a user may rotate the needle hub so that a plurality of granules on the hub will be departed from the hook portion. Thereby, the needle hub can be pulled back into the barrel, and an oblique flexible rod at the front end of the conic head will tilt the needle hub and the needle into an oblique configuration and therefore cannot be used again.

The safety syringe of rotational contraction of the prior art has the following disadvantages. The hook stricture for preventing a departure of the needle hub from the barrel is locked in a groove of granular structure, which is quite a complex design. It is further complicated by the engagement between the projected teeth on the conic head and the holes within the hub. Such a complicated design is difficult to make by plastic injection molding.

Further, as the flexible rod is entering, the attack angle of the rod should be controlled with precision so as to avid hitting the inner wall of the barrel and gets deflected. To achieve the goal of tilt the needle hub the projected teeth on the conic head should be precisely coupled with the holes of the hub, which is too complex a structure.

SUMMARY OF THE INVENTION

Accordingly, the primary objective of the present invention is to provide a plunger of a syringe and a syringe uses the same. The plunger is characterized by a hook unit formed integrally at the front end of the stopper of thereof. The hook unit comprises a central rod and a push wing extended outwardly from a lateral wall of the central rod. The push wing can be attached to the central rod by a lateral force, which is urged during an insertion process, so that the hook unit will be inserted into a receptacle formed at the rear end of the needle hub in the axial direction. The receptacle has an entrance hole and a cavity lager then the hole, whereby the flexible push wing will be extended again after the unit is in the cavity, forming a locked configuration. As the plunger is pulled back, the needle mount will be pulled into the needle barrel accordingly, achieving a function of self destruction.

Furthermore, the present invention further provides a syringe. The syringe comprises a needle barrel being a hollow cylinder provided with a needle hub in a front end thereof, the needle hub further including a needle mount, a needle inserted at a front end of the needle mount along the axis of the needle mount and a receptacle formed at a rear end of the needle mount, a rear end of the needle barrel being provided with a finger flange; and a plunger contained in the needle barrel and provided with a hook unit being a rod body, the hook unit further including a central rod and a push wing extended backward from a lateral wall of the central rod, whereby the push wing will be flexibly attached onto the central rod when the hook unit is driven into a receptacle formed at a base of the needle at a front end of the needle barrel. The needle will be drawn into the needle barrel when the plunger is pulled backward.

The various objects and advantages of the present invention will be more readily understood from the following detailed description when read in conjunction with the appended drawings.

BRIEF DESCRIPTION OF THE DRAWINGS

FIG. 4 is a side cross-sectional view of the syringe in FIG. 1 before the plunger is pulled back along the barrel.

FIG. 5 is a side cross-sectional view of the syringe in FIG. 1 after the plunger is pulled back along the barrel.

DETAILED DESCRIPTION OF THE PREFERRED EMBODIMENTS

Figure 1:
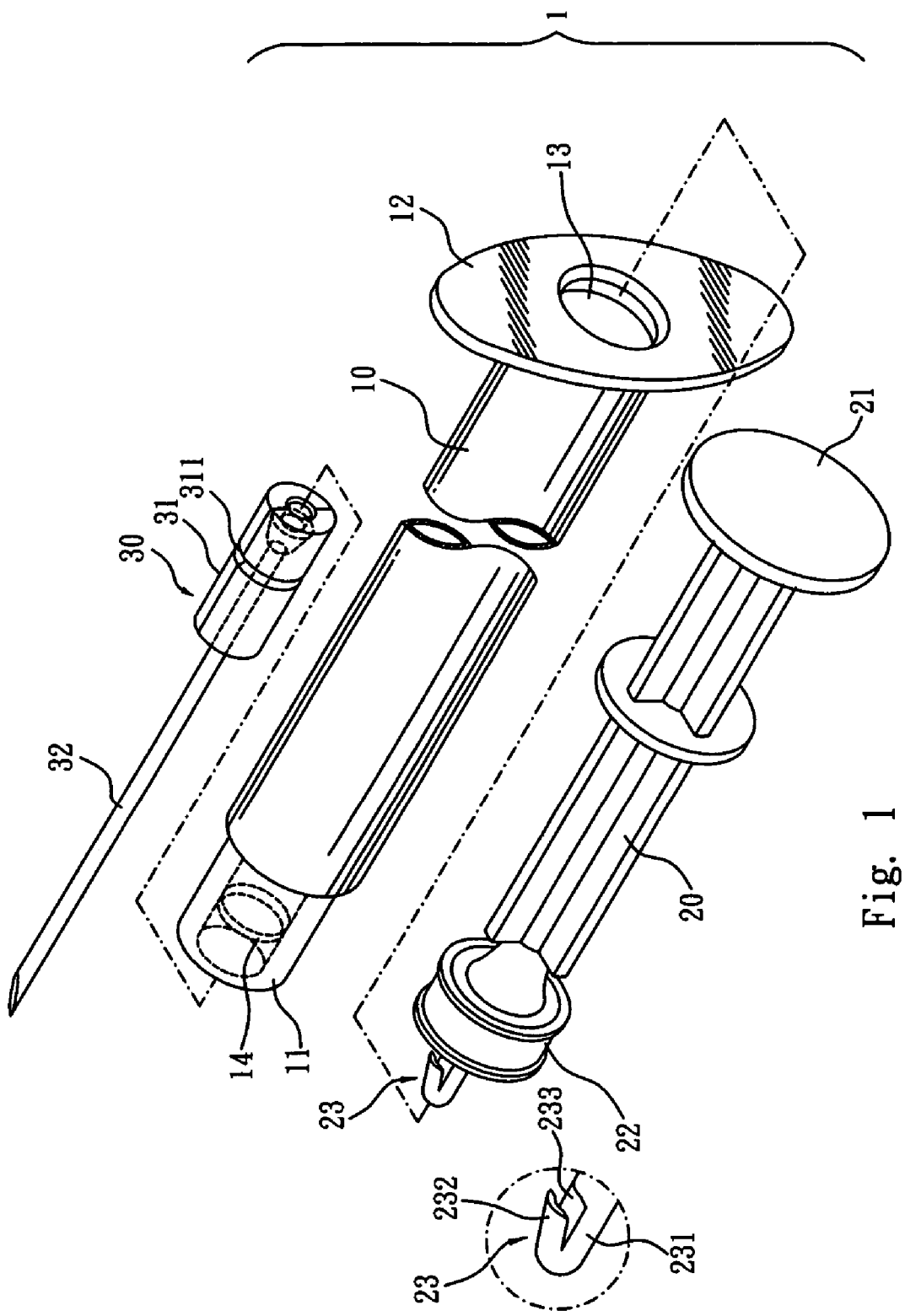
FIG. 1 is an exploded perspective view of a syringe using the present invention.

Referring to FIG. 1, a plunger of a syringe and a syringe uses the same comprises a needle barrel 10, a plunger 20 and a needle unit 30. The needle barrel 10 is a hollow cylinder, and a needle hub 11 is installed at the front end of the needle barrel 10. The needle barrel 10 further includes a finger flange 12 being an enlarger portion at the rear end thereof. Inside the needle hub 11 of the needle barrel 10, there is a receptacle 13 open at two ends. The inner wall of the receptacle 13 is further provided with an annular flange 14 for securing the needle hub 11.

The plunger 20 is inserted into the needle barrel 10 at the end of the finger flange 12, capable of sliding back and forth along the receptacle 13. The rear end of the plunger 20 forms a thumb rest 21 that is larger than the plunger 20 and the receptacle 13. The front end of the plunger 20 is provided with a stopper 22, and the front of the stopper 22 integrally formed a hook unit 23 being a rod body. The hook unit 23 further incuse a central rod 231 and a push wing 232 extended from a lateral wall of the central rod 231. Between the central rod 231 and the push wing 232, there is a wedged empty space 233, resulting from the outward extension of the push wing 232.

The hook unit 23 is an integral part extended outwardly from the stopper 22, and the push wing 232 is an obliquely backward extension from the top of the central rod 231, whereby an empty space 233 will be defined by the two parts. As the push wing 232 is urged by a lateral force, the two parts get closer and the empty space 233 may vanish eventually.

The needle unit 30 includes a needle mount 31 being a round slug and a needle 32. The outer wall of the needle mount is provided with a positioning groove 311 for securing the flange 14 within the needle hub 11. The rear end of the needle unit 30 in the axial direction is provided with a receptacle 13 for receiving the hook unit 23 when unit is inserted therein.

Figure 2:
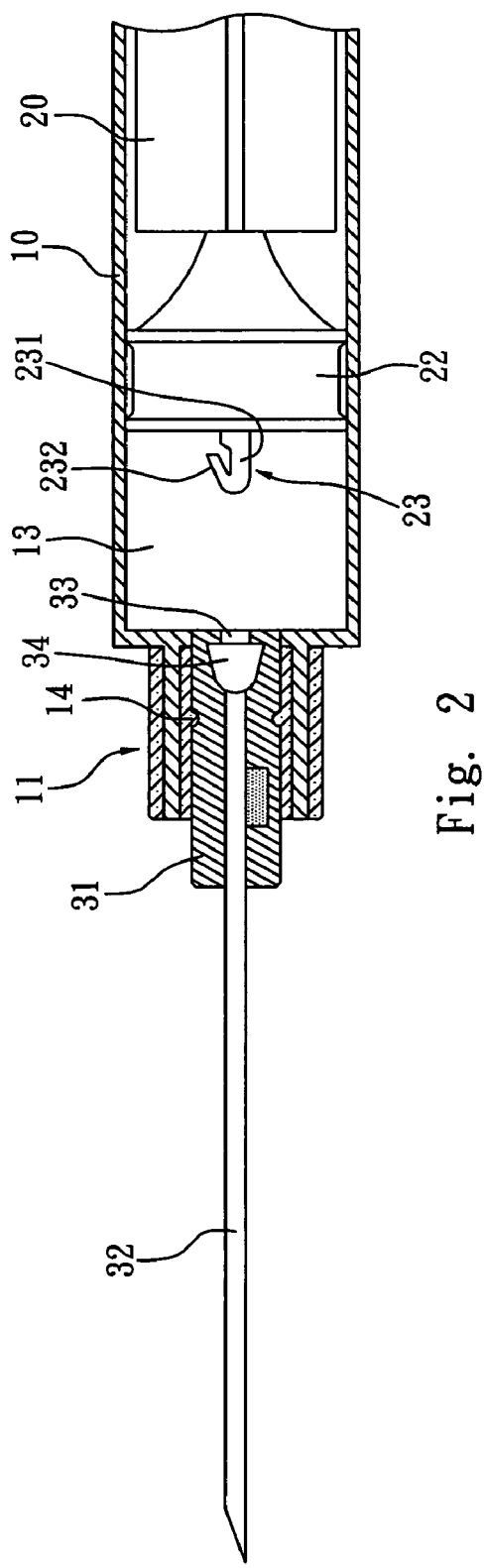
FIG. 2 is a side cross-sectional view of the syringe in FIG. 1 before the hook unit is inserted into the needle hub.
Figure 3:
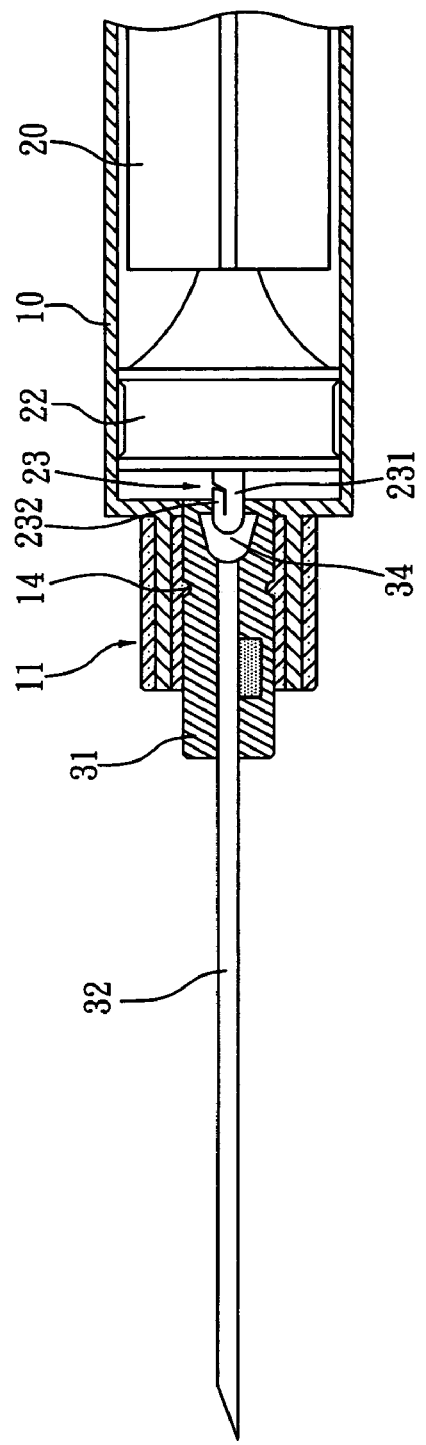
FIG. 3 is a side cross-sectional view of the syringe in FIG. 1 after the hook unit is inserted into the needle hub.

Referring to FIGS. 2 and 3, the receptacle 13 includes an entrance hole 33 and a terminal cavity 34 that is large then the hole 33 and expands inwardly. The entrance hole 33 has a radius slightly larger than outer radius of the hook unit 23 when its push wing 232 and its central rod 231 are firmly attached. Thereby, when the hook unit 23 is passing the entrance hole 33, the push wing 232 is attached onto the central rod 231. After the hook unit 23 is inserted into terminal cavity 34 of the receptacle 13, the hook unit 23 is in the relaxed state, wherein the push wing 232 is supported against the inner wall of the receptacle 13. The central rod 231 has a larger lower end and a smaller upper end so as to receive the push wing 232 so that the push wing 232 will be flexibly attached onto the central rod 231 when the hook unit 23 is driven into a receptacle 13 formed at a base of the needle at a front end of the needle barrel 10. The central rod 231 is approximately vertical to an end surface of a stopper 22 at a front end of the plunger 20 and the hook unit 23 is an integral part extended outwardly from the stopper 22.

Referring to FIG. 4, since the cross section of the terminal cavity 34 is larger than that of the entrance hole 33, the hook unit 23 passing through the entrance hole 33 will be free from a lateral force and become relaxed, wherein the push wing 232 of the hook unit 23 will tilt against the inner wall of the terminal cavity 34. Thereby, the plunger 20 will drag the needle hub 11 when it is pulled backward.

Referring to FIG. 5, as the plunger 20 is pilled backward, the hook unit 23 in the front of the plunger 20 is coupled with the receptacle 13 of the needle mount 31 and thereby the needle mount 31 will go with the plunger 20 and will depart from the needle hub 11. Once departed, the hook unit 23 will further exerts a deflecting force on the needle mount 31, whereby the needle 30 within the needle barrel 10 will be misaligned. Therefore, the needle structure will be ruined as the plunger 20 is pushed toward the front end of the needle barrel 10 again.

The present invention utilizes a hook unit 23 and a needle mount 31 with a receptacle 13, which is a simple, reliable structure for retracting and destroying a needle. Therefore, the manufacturing difficulty and cost can be effectively reduced, and therefore its compositeness in the market is enhanced.

It should be noted that the push wing 232 and the central rod 231 of the hook unit 23 should be an integral part, not appropriate using separated parts connected together. A hook unit 23 wherein the push wing 232 and the central rod 231 are separated parts which are easy to fall apart.

The present invention is thus described, and it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A plunger of a syringe, contained in a needle barrel of a syringe, comprising:
    a hook unit having a central rod and a push wing extended backward from a lateral wall of said central rod, whereby said push wing will be flexibly attached onto said central rod when said hook unit is driven into a receptacle formed at a base of said needle at a front end of said needle barrel, and whereby said needle will be drawn into said needle barrel when said plunger is pulled backward; and
    wherein, as said push wing is relaxed with respect to said central rod, a radius defined by the minimal distance between an axis of said central rod and an outmost edge of said push wing is slightly larger than a radius defined by the minimal distance between the center of an entrance hole of said receptacle and an outmost boundary of a terminal cavity of said receptacle; and
    wherein said push wing will be attached onto said central rod to form a hook unit by a lateral pressure force, whereby the largest radius thereof will be larger than the inner radius of said entrance hole of said receptacle; and
    wherein said central rod has a larger lower end and a smaller upper end, the smaller upper end is connected to the push wing, and the push wing extends from the small upper end of the central rod towards the larger lower end so that said push wing will be flexibly attached onto said central rod and is flushed with outer side of the larger end of the central rod when said hook unit is driven into a receptacle.

2. The plunger of a syringe of claim 1 wherein a wedged empty space is defined between said central rod and said push wing.

3. A syringe, comprising:
    a needle barrel being a hollow cylinder provided with a needle hub in a front end thereof, said needle hub further including a needle mount, a needle inserted at a front end of said needle mount along the axis of said needle mount and a receptacle formed at a rear end of said needle mount, a rear end of said needle barrel being provided with a finger flange; and
    a plunger contained in said needle barrel and provided with a hook unit being a rod body, said hook unit further including a central rod and a push wing extended backward from a lateral wall of said central rod, whereby said push wing will be flexibly attached onto said central rod when said hook unit is driven into a receptacle formed at a base of said needle at a front end of said needle barrel;
    whereby said needle will be drawn into said needle barrel when said plunger is pulled backward; and wherein said central rod has a larger lower end and a smaller upper end, the smaller upper end is connected to the push wing, and the push wing extends from the small upper end of the central rod towards the larger lower end so that said push wing will be flexibly attached onto said central rod and is flushed with outer side of the larger end of the central rod when said hook unit is driven into a receptacle, wherein the central rod is approximately vertical to an end surface of a stopper at a front end of said plunger and said hook unit is an integral part extended outwardly from the stopper.

4. The syringe of claim 3 wherein an inner wall of said needle hub is provided with an annular flange and wherein an outer wall of said needle mount is provided with a positioning groove corresponding to said annular flange.

5. The syringe of claim 3 wherein said receptacle consists of a terminal cavity and an entrance hole.

6. The syringe of claim 3 wherein, as said push wing is relaxed with respect to said central rod, a radius defined by the minimal distance between an axis of said central rod and an outmost edge of said push wing is slightly larger than a radius defined by the minimal distance between the center of an entrance hole of said receptacle and an outmost boundary of a terminal cavity of said receptacle.

7. The syringe of claim 3 wherein said push wing will be attached onto said central rod to form a hook unit by a lateral pressure force, whereby the largest radius thereof will be larger than the inner radius of said entrance hole of said receptacle.

* * * * *